United States Patent [19]
Wilkes

[11] 3,931,332
[45] Jan. 6, 1976

[54] STABILIZED HYDROFORMYLATION REACTION SYSTEMS
[75] Inventor: John B. Wilkes, Richmond, Calif.
[73] Assignee: Chevron Research Company, San Francisco, Calif.
[22] Filed: June 4, 1973
[21] Appl. No.: 367,049

Related U.S. Application Data
[63] Continuation of Ser. No. 878,599, Nov. 20, 1969, abandoned.

[52] U.S. Cl. ...... 260/604 HF; 260/598; 260/632 HF
[51] Int. Cl.$^2$ .......................................... C07C 45/08
[58] Field of Search ............................. 260/604 HF

[56] References Cited
UNITED STATES PATENTS

| | | | |
|---|---|---|---|
| 3,278,612 | 10/1966 | Greene | 260/604 HF |
| 3,594,425 | 7/1971 | Brader et al. | 260/604 HF |

FOREIGN PATENTS OR APPLICATIONS

| | | | |
|---|---|---|---|
| 1,527,562 | 4/1968 | France | 260/604 HF |

OTHER PUBLICATIONS

Iwanaga et al., Chem. Abstracts, Vol. 56, 1962, Col. 10962.

Iwanaga, R. I., Chem. Abstracts, Vol. 57, 1962, Col. 9656.

Primary Examiner—James O. Thomas, Jr.
Assistant Examiner—R. H. Liles
Attorney, Agent, or Firm—G. F. Magdeburger; John Stoner, Jr.; T. G. De Jonghe

[57] ABSTRACT

In hydroformylation reactions at temperatures in the range 100°–225°C. the destructive dissociation of cobalt carbonyl complex compounds to cobalt metal and residue is inhibited by the presence of minor amounts of 2,2'-bipyridine, alkyl-substituted 2,2'-bipyridines, N-alkyl-substituted alkylene diamines and mixtures of these compounds.

6 Claims, No Drawings

STABILIZED HYDROFORMYLATION REACTION SYSTEMS

This is a continuation of application Ser. No. 878,599, filed Nov. 20, 1969, now abandoned.

FIELD OF THE INVENTION

This invention relates to improved hydroformylations of unsaturated organic compounds in which the reaction is catalyzed by a cobalt carbonyl complex compound. More particularly, it relates to a method for the stabilization of cobalt carbonyl complex compounds in a hydroformylation reaction system effected by the action of a small amount of a diamine inhibitor. Still more particularly, this invention relates to the use of particular diamine compounds as catalyst stabilizers in the production of alcohols and/or aldehydes from olefinically unsaturated organic compounds by the cobalt carbonyl catalyzed addition reaction of carbon monoxide and hydrogen to the carbon-to-carbon linkage(s) of these unsaturated compounds.

BACKGROUND OF INVENTION

Cobalt carbonyl compounds including dicobalt octacarbonyl, cobalt hydrocarbonyl etc. as such or in modified forms are known for their use as catalysts for a variety of reactions relating to olefinic unsaturated organic compounds including the hydroformylation (oxonation) of olefins, isomerization of olefins, carbonylation of amines and aromatic nitriles, hydrosilation of olefins and the like. These catalyst complexes are subject to serious limitations in that unless carbon monoxide pressures in excess of cobalt carbonyl complex equilibrium values are maintained in their presence, a destructive dissociation into cobalt metal and residue occurs under hydroformylation conditions. Catalytic acitivity is thus lost and cobalt metal is plated-out on reactor walls and associated transfer piping. From time to time the accumulated metal must be removed by a suitable means, usually by the use of aqueous nitric acid or a similar undesirably corrosive and inconvenient agent.

The suggestion has been made in the art (see, for example, Belgian Patent No. 700,691) that polyamines and related dibasic aromatic compounds are useful in hydroformylation reactions for the stabilization of cobalt carbonyl catalysts provided at least 0.5 mol of the stabilizer be employed for each mol of cobalt in the catalyst. Such relatively large amounts of the nitrogen compounds in general appear to be required for effective stabilization but such use is disadvantageous for many reasons, including cost, side reactions involving the aldehyde and amine functionalities, i.e., condensations which produce byproduct and the like; as well as the need for the use of more severe reaction conditions (higher temperatures and pressures in particular) in order to force the desired reaction to proceed.

It has now been found that the contacting of a cobalt carbonyl complex catalyst with substantially less than the stoichiometric amount, in fact a minor amount, of a bipyridine compound and/or of an N-alkyl alkylenediamine and mixtures thereof, effectively inhibits the destructive dissociation of the catalyst to cobalt metal and/or inhibits the plating-out of cobalt metal on the interior surfaces of a hydroformylation reactor at a temperature in the range from about 100°C. to 225°C. An amount of the stabilizer in the range 0.001 to 0.45, preferably 0.1 to 0.25, mol per mol of cobalt in the catalyst inhibits destructive dissociation of the catalyst and the plating-out of cobalt metal on the interior reactor surfaces. Surprisingly, the presence of these inhibitors permits the employment of carbon monoxide pressures well below conventional equilibrium pressures for cobalt carbonyl complex compositions. A yet further advantage of the present process is found in the fact that with the substantial reduction in carbon monoxide pressures made possible by the instant stabilizers, both hydroformylation and hydrogenation can be carried out in a single reactor and/or with but a single catalyst system. Compounds suitable for use in the present invention are 2,2'-bipyridines of the formula

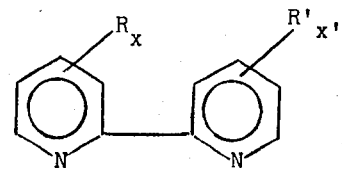

in which R and R' are the same or different alkyl groups having a carbon atom content less than 25, $x$ and $x'$ are the same or different and are 0 or 1, and the alkyl groups may be located at any position except at the 1,2,1' and 2' positions; N-alkyl substituted alkylene diamines of the formula

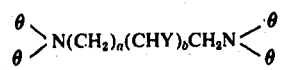

in which the $\theta$ are the same or different and are hydrogen or alkyl groups having a carbon atom content less than 25. At least one of the groups $\theta$ must be an alkyl group. The sum of the subscripts $a$ and $b$ must be 1 or 2 and $a$ may be 0, 1 or 2 and $b$ may be 0 or 1, and in which Y is an alkyl group having a carbon atom content less than 25; and mixtures of the foregoing compounds. Preferred alkylene diamine-type inhibitors are of the formula

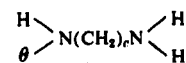

in which $c$ is 2 or 3 and $\theta$ is an alkyl group having a carbon atom content in the range from 10 to 25.

In a preferred embodiment a straight chain alphaolefin hydrocarbon feed, for example 1-dodecene, carbon monoxide, hydrogen, cobalt octacarbonyl and 2,2'-bipyridine are charged to a pressure reactor maintained at about 190°C. Based upon the olefin feed about 0.2 weight per cent of the catalyst (calculated as cobalt metal) and about 0.1 mol of the bipyridine per mol of the cobalt are used. The total pressure in the reaction system is maintained in the range 1000–2200 psig with the mol ratio of hydrogen to carbon monoxide being about 2 to 1, respectively. After about 120 minutes at pressure and temperature the conversion of the olefin feed is essentially complete and the product is mainly alkanol. Little or none of the cobalt carbonyl complex catalyst is converted to metal in the course of the reaction. What metallic solid as may be formed is present in the form of a loose powder rather than as a metal plate adhering to the reactor surfaces.

Hydroformylation reactions may be illustrated by the general equation:

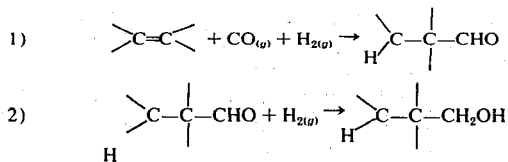

wherein the unsatisfied valence bonds are attachments to the atoms or radicals necessary to complete the olefinic compound. Substantial partial pressures of carbon monoxide and hydrogen are required for the reaction to proceed with suitable relative proportions of hydrogen to carbon monoxide being in the range 0.5–10 to 1 respectively, and preferably 1–3 to 1. Normally in the absence of a suitable catalyst stabilization means, satisfactory total pressures (carbon monoxide plus hydrogen) are in the range 700 to 10,000 psig with corresponding temperatures being in the range 140° to 250°C. The present stabilizers permit satisfactory operation at system pressures in the range from about 50 psig to up to about 4000–5000 psig with the corresponding temperatures being about 75° to 225°C., preferably 125° to 200°C.

By a hydroformylation reactor, as used herein, is meant pressure reactors, autoclaves and the like, as known in the art.

In the absence of a suitable stabilization means cobalt carbonyl complex compounds equilibrate into a system which contains many members, including dicobalt octacarbonyl, cobalt hydrocarbonyl, the salt Co[Co(CO)$_4$]$_2$, etc. Any and all of these complex compounds are either useful hydroformylation catalysts per se or are catalyst precursors. Cobalt metal may also be a member of the above noted equilibrium set. However, in hydroformylation reactions for all practical purposes the formation of cobalt metal is an irreversible reaction and one to be avoided. Usually it is more convenient to prepare the catalyst in situ by the reaction of cobalt oxide, a cobalt salt or soap with hydrogen and carbon monoxide in the vessel contemplated for use in a hydroformylation reaction.

The medium for the in situ preparation in general comprises a liquid reactant, for example an unsaturated organic compound or an olefinic hydrocarbon, from a reaction system for which the cobalt carbonyl complex is to serve as a catalyst. Inert liquid media or diluents such as saturated hydrocarbons, aromatic hydrocarbons, alcohols, high-boiling reaction by-products, etc. as known in the art may also be employed.

In general, best results in terms of stabilization effects obtain when the stabilizers of the present invention are present initially, although good results are also experienced from a subsequent addition. Other stabilizers such as organophosphine compounds are known in the art. However, in the use of these materials substantially stoichiometric amounts and more of these compounds are required. Phosphines in general are toxic and costly, a factor which seriously limits their utility. Preferably one or more of the subject compounds are the sole stabilization means other than carbon monoxide in the reaction system.

In the active form, the stabilized cobalt carbonyl catalyst will contain most of the cobalt component in a reduced valence state, usually zero or possibly even a -1 valence.

As used herein, the term "complex compound" relates to combinations of two or more atoms, ions, or molecules which arise as a result of the formation of a bond(s) by the sharing of a pair(s) of electrons originally associated with only one of the components, and the complex possesses identifiable physical or chemical characteristics of a distinct species.

The relative amount of the stabilizer which should be employed varies, depending upon the particular reaction conditions being employed. At the lower reaction temperatures relatively smaller amounts are satisfactory. Similarly, for a given reaction temperature as the carbon monoxide partial pressure is increased, relatively smaller amounts of the bipyridine agent are required for satisfactory stabilization. In general, the amount of the agent used will be in the range from about 0.001 to 0.45 mol per mol of cobalt in the reaction system. Usually better results obtain when the ratio is substantially less than stoichiometric, i.e., in the range from about 0.1–0.25 to 1 respectively.

The amount of catalyst desirably employed in the present process corresponds to prior art requirements. Usually catalyst concentrations, based upon the olefinically unsaturated feed (weight percentages) and calculated as cobalt metal in the range 0.05 to 5.0 weight percent are satisfactory. Preferred amounts are in the range 0.1 to 0.5.

Olefinically unsaturated organic compounds as known in thy hydroformylation (oxo) art are, in general, satisfactory feeds for use in the present invention. Preferred feeds are monoolefinic hydrocarbons. Of these, linear olefins of the C$_3$ to C$_{20}$ range, propylene oligomers and the like, are the most desirable feeds. Where branched chain olefins are used for the production of oxo-alcohols, it is often more advantageous to effect the carbon monoxide-hydrogen addition to the olefinic double bond at about 140°–170°C. and to subsequently heat the reaction mixture to a higher temperature (180°–210°C.) where the reduction of the aldehyde group proceeds more favorably.

Representative olefinic hydrocarbons suitable for use herein include ethene, propene, 1-hexene, cyclohexene, betapinene, alpha-pinene, 2-heptene, 3-ethylpentene-1, 2-methylpentene-2, cyclopentene, di-isobutylene, propylene trimer, codimer heptenes, vinylcyclohexene, cyclododecene, 3-eicosene, 1-dodecene and the like olefinic hydrocarbons.

The 2,2'-bipyridine and N-alkyl alkylenediamines formulated above are in general contemplated for use as catalyst stabilizers in the process of the present invention. The alkylenediamines are preferred for reasons of cost and availability.

Representative bipyridine stabilizer compounds useful in the practice of the invention include 2,2'-bipyridine, 4,4'-dimethyl-2,2'-bipyridine, 3,4'-, 5,5'-, and 6,6'-dimethyl-2,2'-bipyridine, 4,4'-di-n-eicosyl-2,2'-bipyridine, 4-(2-octyl)-2,2'-bipyridine, 5,5'-di-t-butyl-2,2'-bipyridine, 6-s-butyl-2,2'-bipyridine, 5,6'-di-n-undecyl-2,2'-bipyridine, and the like alkyl-2,2'-bipyridines. (See, for example, British Patent No. 955,951 which discloses a convenient process for the preparation of alkyl-2,2'-bipyridines.)

Representative N-alkyl alkylenediamines useful in the practice of this invention include
N-Octadecyl-propane-1,3-diamine,
N-Eicosyl-ethylenediamine, N-Octadecyl-isobutylenediamine,
N,N'-Dioctadecyl-ethylenediamine,
N,N,N'-Triundecyl-propane-1,3-diamine,
N,N'-Diisopropylethylenediamine,
N-Nonylpropane-1,3-diamine,
N-Decylpropane-1,2-diamine,
N-Hexadecylhexadecane-1,2-diamine,
N-Pentacosanyl-propane-1,3-diamine,
N-Tricosanyl-ethylenediamine,
N-Methyl-N-octadecylethylenediamine,
N-Methyl-N-pentacosanyl-propane-1,3-diamine,
N-Methyl-N-tetradecyl-propane-1,3-diamine,
N-Methyl-N-pentadecyl-propane-1,3-diamine,
N-Methyl-N-hexadecyl-propane-1,3-diamine,
N-Ethyl-N-heptadecyl-propane-1,3-diamine,
N-Ethyl-N-octadecyl-propane-1,3-diamine,
N-Methyl-N-nonadecyl-propane-1,3-diamine,
N-Methyl-N-octadecyl-propane-1,2-diamine,
N-Octadecyl-pentacontane-1,2-diamine,
N-Octadecyl-pentadecane-1,3-diamine, and
N-Octadecyl-2-octylpropane-1,3-diamine.

COBALT CARBONYL STABILITY TEST

The stabilizing action of the inhibitors of the present invention upon complex cobalt carbonyl compounds is shown by means of a suitable test. The relative stabilizing action is shown by comparative examples subjecting them to a standard set of conditions with and without the added ligand. These conditions include:

| | |
|---|---|
| Temperature, °C. | 190 |
| Time, hrs. | 6 |
| Solvent | Mixed alcohol-alkane[1] |
| $H_2$:CO mol ratio | 2:1 |
| Pressure, psig | 1600–1800 |

[1]All runs with 0.236 grams of cobalt as octanoate in 50 g n-heptane and 50 g $C_{12}$–$C_{15}$ oxo alcohol.

The test is carried out in a stainless steel rocking autoclave having a glass liner. Under these conditions cobalt salts such as cobalt 2-ethylhexanoate are rapidly converted to complex cobalt carbonyls. Therefore, as a matter of convenience, the salt rather than the carbonyl compound is charged to the autoclave. After the 6 hours at temperature with agitation, the autoclave and contents is cooled to room temperature and vented. The solution is then filtered and analyzed for cobalt carbonyl by infrared absorption at 2041 $cm^{-1}$. Metallic solid if present and its form is noted. In the absence of stabilizers and under the foregoing conditions all of the cobalt carbonyl is converted to a cobalt metal plate which is found adhering to the walls of the glass liner and autoclave. In the presence of an effective stabilizer, little or no metal plating-out occurs, or but small amounts of filterable metal powder are formed. With stabilizers of intermediate effectiveness, little or no metal is found in the liner; but metal is found outside the liner, either deposited on the external liner wall or the autoclave wall, or loosely lodged between the liner and the autoclave wall. Decompositions outside the liner appear to be due to the higher temperatures which exist at the autoclave wall because of the proximity of the heating element and the low level of the stabilizer. The stabilizer inhibits decomposition of the cobalt carbonyl in the solution inside the liner, but does not prevent some diffusion through the vent holes in the liner into the void between the liner and the autoclave inner wall. In Table I below is listed a number of representative test results.

TABLE I

AMINE STABILIZERS FOR HYDROFORMYLATION SYSTEMS

| | Stabilizer | | | | Cobalt as $Co_2(CO)_8$, | |
|---|---|---|---|---|---|---|
| No. | Type | Wt. % of[1] Solution | Moles Per Mole Co. | Pressure Psig | % of Cobalt Fed | Observations |
| 1 | None | — | — | 1650 | 0 | Metal plate on liner walls. |
| 2 | Pyridine | 0.16 | 0.50 | 1700[2] | 0 | Metal plate on liner walls. |
| 3 | 2,2'-Bipyridine | 0.033 | 0.05 | 1675 | 69 | Trace of red solid. |
| 4 | N-Octadecylpropane-1,3-diamine | 0.35 | 0.25 | 1800 | 69 | Trace of metal outside liner. |
| 5 | Ethylene diamine | 0.045 | 0.19 | 1750 | Trace | Metal plating inside and out of liner. |
| 6 | 1,3-Propanediamine | 0.075 | 0.25 | 1800 | Trace | Metal plate in liner. |
| 7 | Diethylenetriamine | ~0.06 | 0.14 | 1730 | Trace | Metal plate in and out of liner. |

[1]All runs with 0.236 grams of cobalt as octanoate in 50 g n-heptane + 50 g $C_{12}$–$C_{15}$ oxo alcohol.
[2]1.3/1, $H_2$:CO The above comparative examples demonstrate that 2,2'-bipyridines and N-alkyl substituted alkylenediamines are effective cobalt carbonyl complex compound stabilizers.

EXAMPLES 8–10

Advantages of the instant process are illustrated by comparative examples in which $C_{13}$–$C_{14}$ alpha-olefin feeds are converted to oxo alcohols in a cobalt carbonyl catalyst hydroformylation using commercial catalyst requirements, e.g., 0.2–0.5 weight per cent of cobalt based upon olefin and other conditions, as noted in Table II below.

TABLE II

| HYDROFORMYLATION TYPE | CONVENTIONAL | | STABILIZED CATALYST[1] | |
|---|---|---|---|---|
| EXAMPLE | 8 | 9 | 10 | |
| HYDROFORMYLATION CONDITIONS | | | | |
| TEMP., °C. | 175 | 200 | 150, | 190[2] |
| PRESSURE, PSIG | 3500 | 4400 | 2000, | 2250 |
| CARBON MONOXIDE | 1550 | 3000 | 670, | 750 |
| HYDROGEN | 1850 | 1400 | 1330, | 1500 |
| TIME, MIN. | — | 180 | 150, | 90 |

TABLE II-continued

| HYDROFORMYLATION TYPE | CONVENTIONAL | | STABILIZED CATALYST[1] |
|---|---|---|---|
| HYDROGENATION CONDITIONS | | NOT NEEDED | NOT NEEDED |
| TEMP., °C. | 140 | — | |
| PRESSURE, PSIG | 1400 | — | |
| YIELDS, WT % OF FEED OLEFIN | | | |
| ALCOHOL | 82 | 85 | 83 |
| PARAFFIN | 8 | 12 | 4 |
| THICK OIL | 16 | 10 | 19 |

[1]2,2'-bipyridine stabilizer, 0.25 mol per mol of cobalt.
[2]Reaction in two stages carried out in same reactor.

From a comparison of Examples 8, 9 and 10 above, it is evident that hydroformylation reactions can be run under substantially lower pressures and in a single reactor when carried out in the presence of the catalyst stabilizers disclosed herein. The N-alkyl-alkylene-diamine stabilizers disclosed herein also effectively stabilize cobalt carbonyl complex compounds in hydroformylation reaction systems.

EXAMPLE 11

Using the same olefin feed and relative proportions of catalyst to olefin, Example 10 was repeated except that:

1. 1.5 mol of the bipyridine inhibitor per mol of cobalt; and
2. the conditions:

| Temperature, °C. | 190 |
|---|---|
| Pressure, psig | 2200 |
| H$_2$:CO, mol ratio | 2:1 | were employed. After a reaction period of 600 minutes the resulting product was as follows:

| | Wt. % of Olefin Feed[1] |
|---|---|
| Alcohol | 5 |
| Aldehyde | 57 |
| Hydrocarbon | 34[2] |
| Thick Oil | 12[3] |

[1]Analyses by gas chromatography using appropriate standards.
[2]Mainly olefin.
[3]By difference.

From a comparison of Examples 10 and 11, it is seen that the presence of a substantial amount of a diamine-stabilizer in a hydroformylation reaction system markedly reduces the reaction rate, (i.e., 240 minutes reaction time for Example 10 versus 600 minutes for Example 11) and interferes greatly with alcohol formation (i.e., 83 weight per cent yield for Example 10 versus 5 weight per cent yield for Example 11).

I claim:

1. In the cobalt carbonyl complex compound catalyzed reaction of a hydroformylatable monoolefinic hydrocarbon with carbon monoxide and hydrogen in a hydroformylation reactor, wherein during the course of said reaction cobalt metal resulting from destructive dissociation of said cobalt compound plates-out on the interior surfaces of said reactor, the improvement which consists essentially of carrying out the reaction at a temperature in the range from 100° to 225°C., with the reactants in contact with a cobalt carbonyl complex compound stabilizer consisting of a diamine of the formula

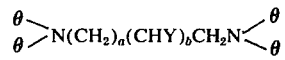

wherein said $\theta$ are the same or different and are selected from the group consisting of hydrogen and alkyl groups having a carbon atom content less than 25; wherein at least one of the $\theta$ is an alkyl group having a carbon atom content in the range from about 10 to 25; wherein Y is an alkyl group having a carbon atom content less than 25; and wherein $a$ is 0, 1, or 2 and $b$ is 0 or 1 with the sum of $a + b$ being 1 or 2; and wherein for each mol of cobalt in the catalyst an amount of the stabilizer in the range from 0.001 to 0.45 mol is present in the reactor and wherein the cobalt catalyst is free of phosphine compounds.

2. The hydroformylation as in claim 1 further characterized in that the amount of the stabilizer is in the range from about 0.1 to 0.25 mol.

3. The hydroformylation as in claim 1 further characterized in that the reaction is effected using two temperature stages, the first of which is in the range from about 140° to 170°C., and the second of which is in the range from about 180° to 210°C.

4. The hydroformylation as in claim 1 further characterized in that the stabilizer is of the formula

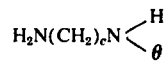

wherein $\theta$ is an alkyl group having a carbon atom content in the range from about 10 to 25 and $c$ is 2 or 3.

5. The hydroformylation as in claim 1 further characterized in that the hydrocarbon is a linear mono-olefinic hydrocarbon having a carbon atom content in the range from about 3 to 20.

6. In the cobalt carbonyl complex compound catalyzed reaction of a hydroformylatable 1-alkene hydrocarbon with carbon monoxide and hydrogen in a hydroformylation reactor, wherein during the course of said reaction cobalt metal resulting from destructive dissociation of said cobalt compound plates-out on the interior surfaces of said reactor, the improvement which consists essentially of carrying out the reaction at a temperature of about 190°C. with the reactants in contact with a cobalt carbonyl complex compound stabilizer consisting of N-octadecyl-propane-1,3-diamine, wherein for each mol of cobalt in the catalyst an amount of the stabilizer in the range from about 0.1 to 0.25 mol is present in the reactor and wherein the cobalt catalyst is free of phosphine compounds.

* * * * *